United States Patent [19]

DiGiovanni et al.

[11] 4,448,194
[45] May 15, 1984

[54] FULL STROKE COMPELLING MECHANISM FOR SURGICAL INSTRUMENT WIHT DRUM DRIVE

[75] Inventors: John DiGiovanni, Irvington; Szabolcs M. Vigh, Woodbridge, both of N.J.; William P. McVay, Clearwater, Fla.; Anthony S. Miksza, Jr., Jersey City, N.J.

[73] Assignee: Ethicon, Inc., Somerville, N.J.

[21] Appl. No.: 345,308

[22] Filed: Feb. 3, 1982

[51] Int. Cl.³ .................. A61B 17/00; A61B 17/12
[52] U.S. Cl. .................. 128/334 R; 128/303 R; 227/DIG. 1; 227/67; 112/80; 81/313
[58] Field of Search .................. 604/57-64; 112/169, 80; 74/575; 81/313; 128/303 R, 334 R; 227/DIG. 1

[56] References Cited

U.S. PATENT DOCUMENTS

| | | | |
|---|---|---|---|
| 2,444,570 | 7/1948 | Lawrence | 74/575 |
| 2,883,984 | 4/1959 | Candido | 604/61 |
| 3,636,782 | 1/1972 | Huber | 74/575 |
| 4,049,177 | 9/1977 | Bussard | 227/DIG. 1 |
| 4,325,376 | 4/1982 | Klieman | 227/DIG. 1 |

Primary Examiner—C. Fred Rosenbaum
Assistant Examiner—Gene B. Kartchner
Attorney, Agent, or Firm—Robert L. Minier

[57] ABSTRACT

An actuating mechanism is provided for a hand-operated surgical instrument having at least one operating member. The operating member is engaged by or extends from a flexible pusher member wound at least partially around the circumference of a drum and secured thereto. A pinion is connected to the drum for rotation therewith and is driven by a gear segment on a handle that is pivotally monted to the instrument. A full stroke compelling mechanism is associated with the drum for preventing return of the handle to the unactuated position unless and until the operating member has been moved through the full design range of movement.

7 Claims, 21 Drawing Figures

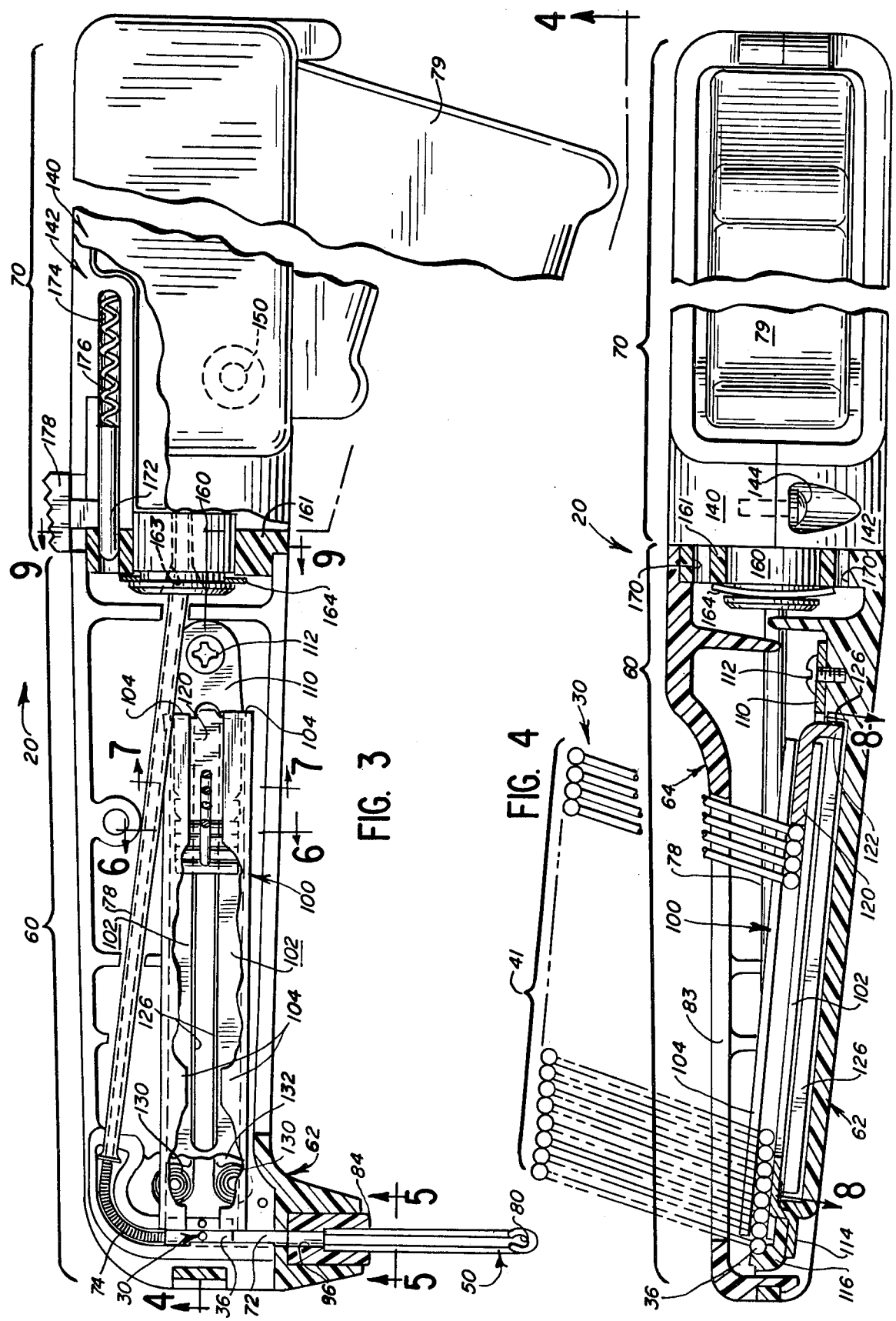

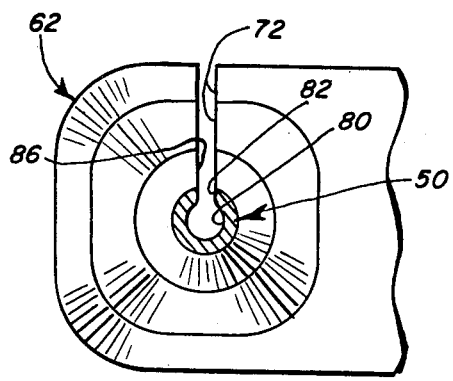
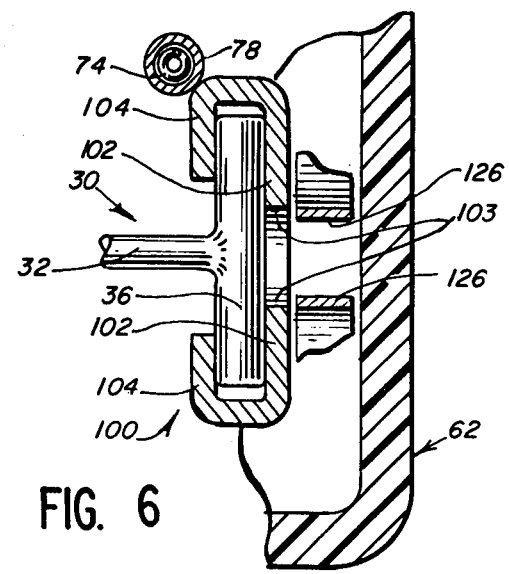
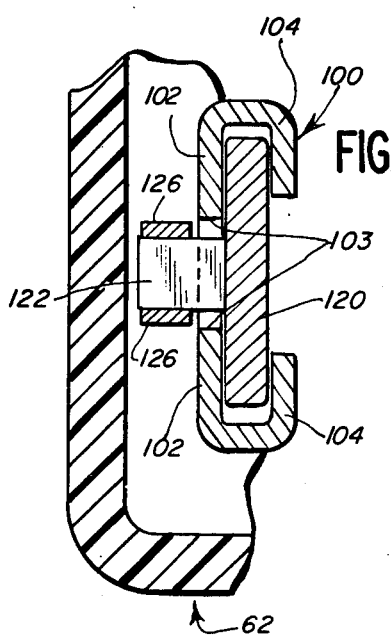
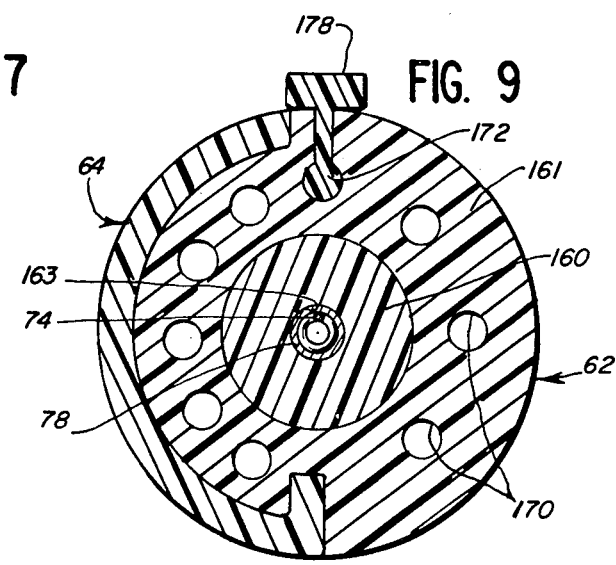
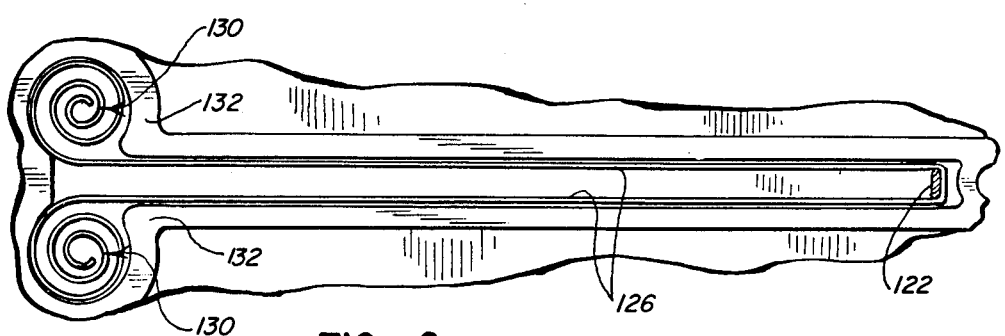

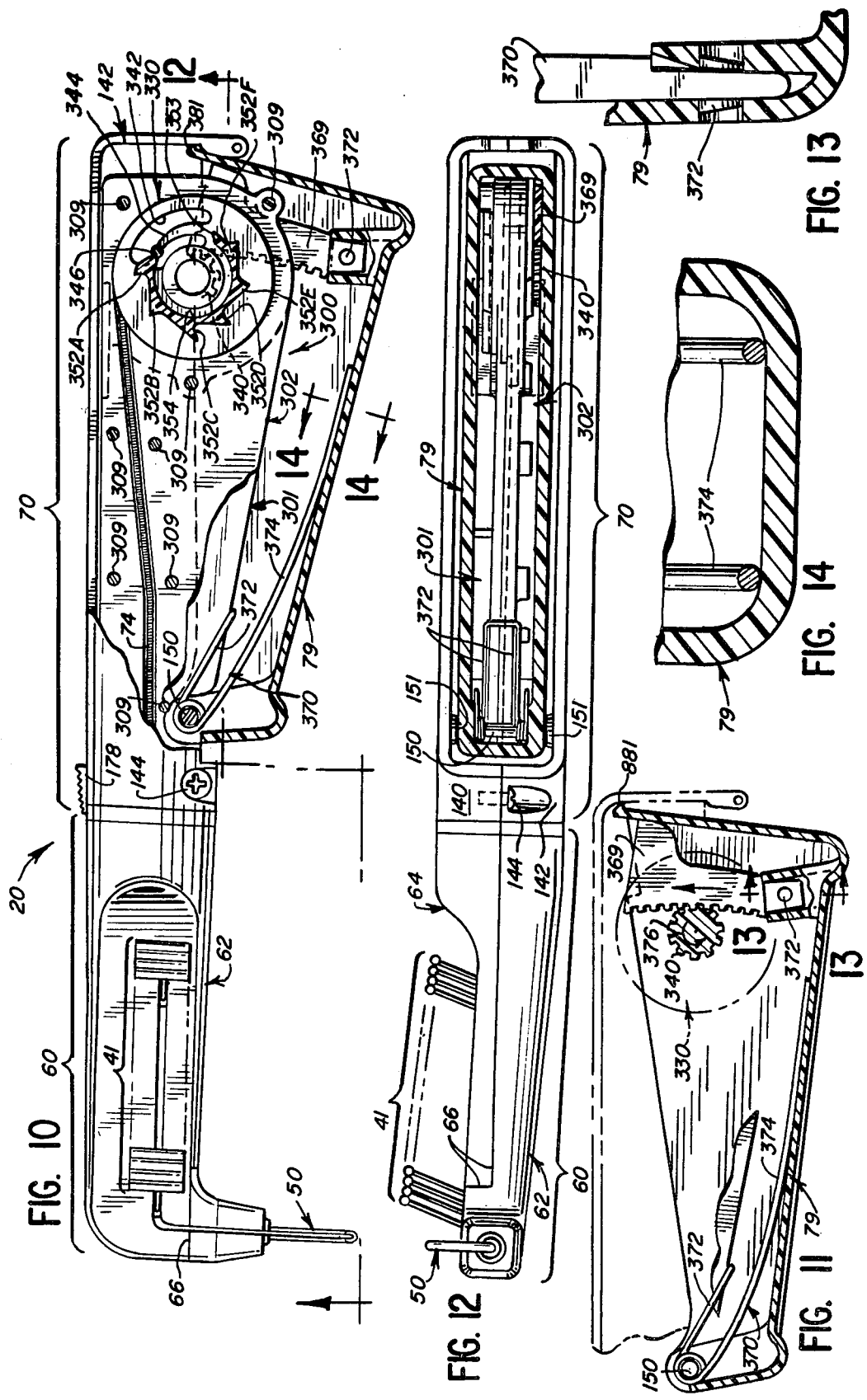

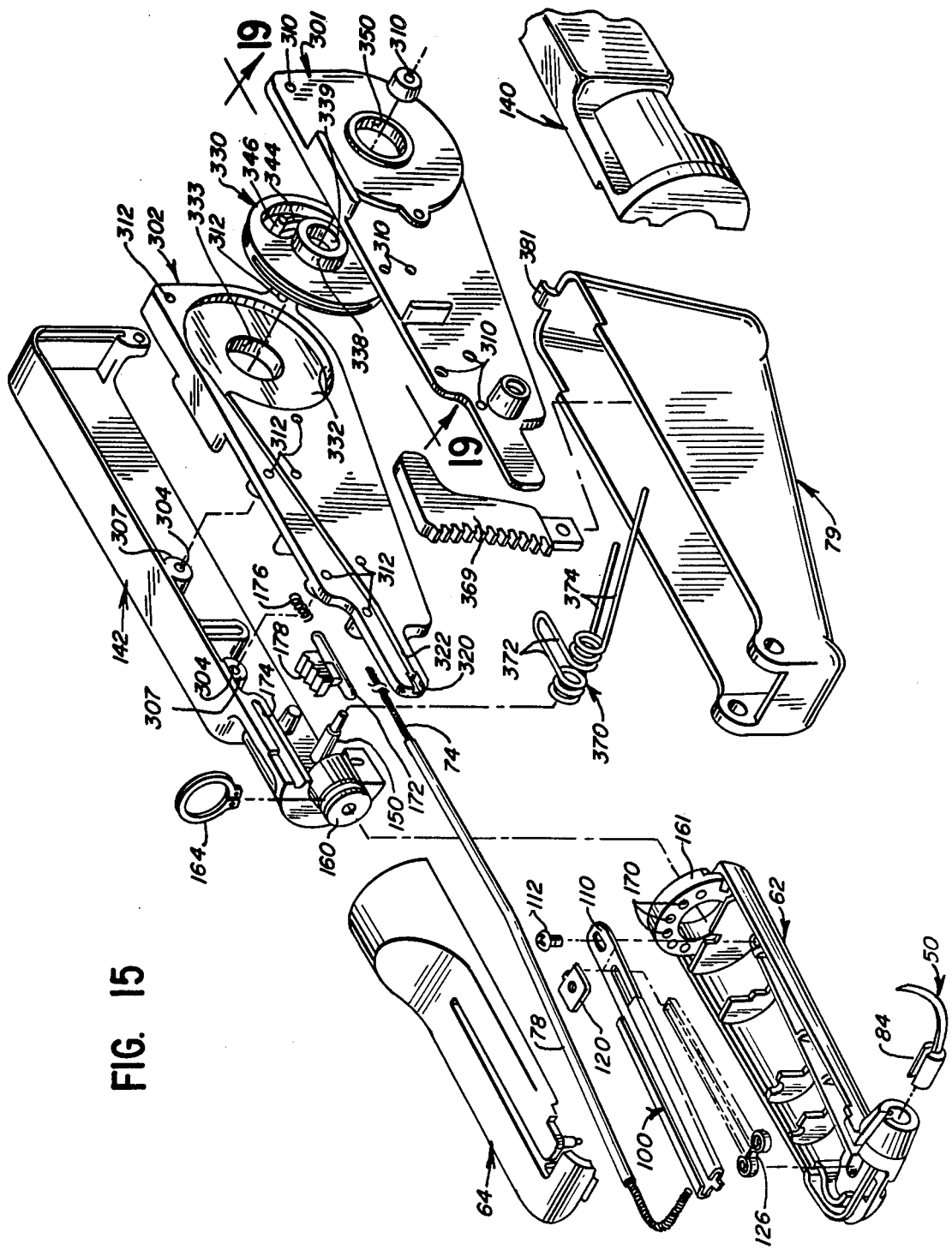

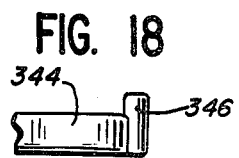
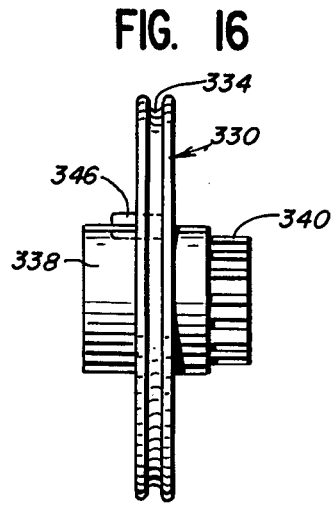
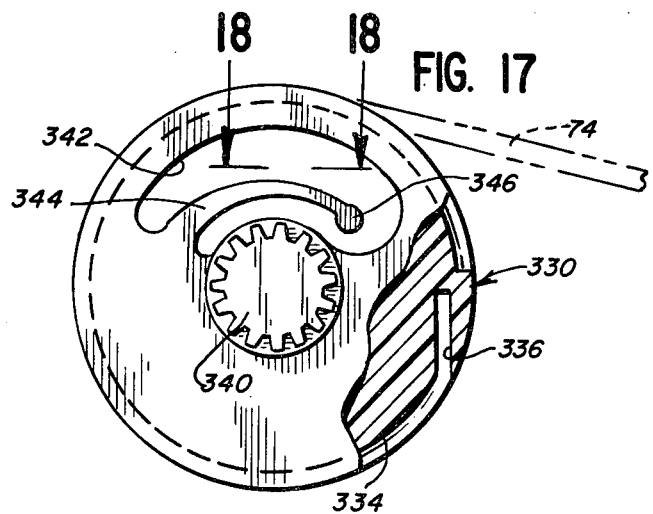
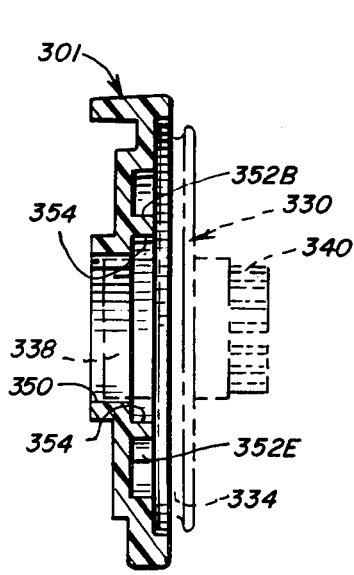
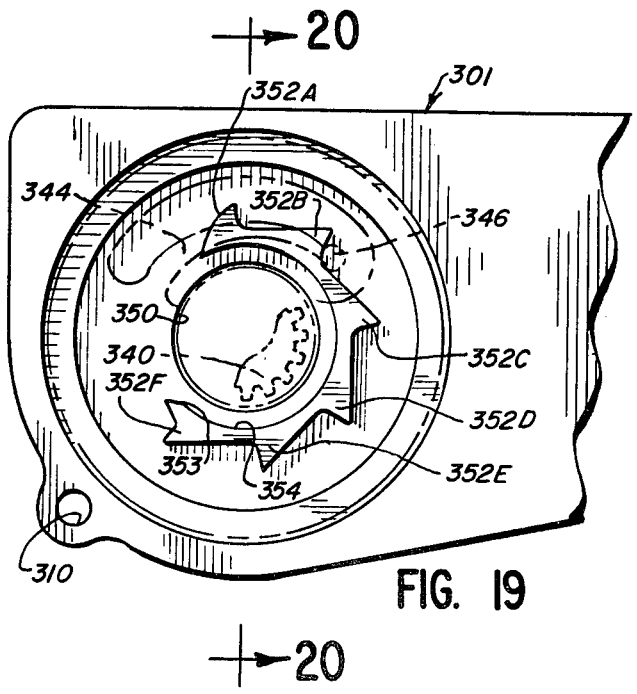

FULL STROKE COMPELLING MECHANISM FOR SURGICAL INSTRUMENT WITH DRUM DRIVE

DESCRIPTION

1. Technical Field

This invention relates to hand-operated surgical instruments, and more particularly to a mechanism for ensuring that a surgical instrument is properly operated.

2. Background of the Invention

A variety of hand-held, hand-operated surgical instruments have been proposed and/or are in use today for effecting a variety of surgical procedures that are performed upon human or animal anatomical structures, such as bone and tissue, including skin, muscle, and fascia. Some of these instruments are also used to effect certain operations with, or on, foreign bodies or prosthetic devices that may be implanted in, or carried by, a human or animal subject. Examples of the above-described instruments include instruments for applying ligating clips to blood vessels, bone crushing instruments, pin cutting instruments, instruments for applying staples or other types of fasteners to tissue, and the like.

Many of these types of instruments are held in one hand by the surgeon and include one or more movable operating elements or members (e.g., crimping or gripping jaws) which are located toward an end of the instrument that is spaced from, or remote from, the surgeon's hand. Typically, such an instrument includes an operating handle mechanism, which may be a reciprocative element, a single lever, a pair of scissors-type levers, or other suitable mechanism. The operating member or members are connected through mechanical linkages to the handle mechanism. Manipulation of the handle mechanism by the surgeon causes the desired movement of the operating member or members so as to effect the desired operation, such as applying a ligating clip to a blood vessel, cutting a pin, crushing a bone, inserting a staple or fastener into tissue, and the like.

A method has been proposed for using an instrument or device for closing wounds or surgical incisions in mammalian tissue with fasteners made from flexible and resilient biocompatible material which may be either absorbable or nonabsorbable in body tissue. One such type of device for applying such a fastener to tissue is generally disclosed in U.S. Pat. No. 4,006,747.

The device disclosed in U.S. Pat. No. 4,006,747 generally includes a slotted hollow needle in which is carried a portion of the fastener, a rigid plunger for pushing the fastener along the needle and into the tissue, and a mechanism for moving the plunger into the needle and then for withdrawing the plunger from the needle.

Other devices of the type disclosed in U.S. Pat. No. 4,006,747 suitable for use in applying various types of fasteners are disclosed in U.S. Pat. Nos. 3,470,834, 3,103,666, 2,069,878, 3,494,004, 3,399,432, 3,518,729, and Design Patent No. 313,418.

Other devices for applying fasteners in a non-surgical situation are disclosed in U.S. Pat. Nos. 3,209,422 and 3,733,657.

Prior to the disclosure in U.S. Pat. No. 4,006,747 of the method for applying a fastener simultaneously through a needle and tissue, procedures for the manual application of sutures or fasteners through tissue with needles or needle-like elements were known. Examples of such sutures and needles are disclosed in U.S. Pat. Nos. 3,636,956, and 3,716,058.

It would be desirable to provide a gear operated mechanical actuating mechanism for use in a wide variety of surgical instruments, including in the fastener applying devices described above. Further, it would be desirable to provide such an actuating mechanism with means for automatically returning the instrument handle mechanism to an unactuated or released position.

In addition, the inventors of the present invention have determined that it would be advantageous if the actuating mechanism could be provided in a surgical instrument, including in a fastener applying device, with means for preventing return of the handle mechanism to a fully released position unless and until the device has first been actuated to effect a complete operation (e.g., a full insertion of a fastener into the tissue).

Also, it would be advantageous if instruments of the class described could be provided with the actuating mechanism of the type described wherein the actuating mechanism was relatively small and compact so as to permit incorporation of the mechanism in a housing that could be easily grasped and manipulated with one hand by the surgeon.

It would be also beneficial if the actuating mechanism could be made from relatively inexpensive materials, along with the other instrument components, so that the instrument, after being initially provided to the surgeon in a sterile package, can be disposed of after one use. With such a disposable instrument, it would be desirable to provide an actuating mechanism that could be fabricated, along with the other components of the instrument, from non-toxic materials that would have little or no deleterious effects on the environment as a result of proper disposal of the instrument after use.

SUMMARY OF THE INVENTION

The present invention provides a novel actuating mechanism for surgical instruments comprising a drum drive for effecting movement of an operating member wherein a full stroke compelling mechanism is associated with the drum drive. In a preferred form disclosed herein, the present invention contemplates a novel actuating mechanism for, and other modifications to, the fastener applying device of the general type disclosed in U.S. Pat. No. 4,006,747.

In general, the novel actuating mechanism can be used in those hand-operated surgical instruments that have at least one movable operating member remote from or extending from a movable handle means for actuating the operating member. The system includes a flexible pusher member that functions as, or is connected to, the movable operating member. A gear operated actuating mechanism is operably connected between the handle means and the pusher member for effecting the movement of the operating member when the handle means is moved relative to the instrument. The system further includes a biasing means for returning the pusher member and the handle means to their unactuated positions.

In a preferred form of the invention, the actuating system is incorporated in a fastener applying device that is adapted for closing a wound or incision in tissue with a fastener. The fastener is of the type comprising a filament member terminated on at least one end by an anchoring means. The other end may also have an anchoring means. The fastener is applied by the device to remain in the tissue with the filament member transversing the wound or incision through the tissue to maintain the tissue in approximation at the wound or incision.

Preferably, the device includes a housing in which, inter alia, the actuating system is disposed. A hollow needle extends outwardly from the housing and has a distal end adapted for piercing the tissue. The needle defines a passage therein for receiving an anchoring means of the fastener. The passage in the needle extends along the length of the needle from an entrance aperture to a discharge aperture at the distal end of the needle. The needle also defines a slot communicating with the passage along the length of the needle from the entrance aperture to the discharge aperture. The slot is adapted to receive a portion of the fastener filament member.

The operating member in the device is in the form of a flexible, elongate pusher member adapted to reciprocate in the needle passage and adapted to engage the anchoring means of the fastener for pushing the fastener along the needle.

The actuating mechanism includes a rotatable drum to which the pusher member is secured and around which it is wound. A pinion is secured to the drum for rotation with the drum. A gear segment is provided to mesh with the pinion and is operably connected to a handle that is pivotally mounted to the device. Movement of the handle effects the desired movement of the pusher member.

The length of the pusher member and the movement stroke effected by the actuating mechanism is selected so that the pusher member can be reciprocated between (1) a retracted position spaced inwardly from the discharge aperture of the needle to permit admission of a fastener into the needle and (2) an extended position outwardly along the needle relative to the retracted position wherein the fastener is ejected from the discharge aperture of the needle by the pusher member.

The actuating mechanism employed in the device includes a novel full stroke compelling mechanism. Specifically, a pawl is provided on the drive drum for engaging teeth on the housing to prevent repeated actuation of the operating member unless and until the pusher member has been moved through the full design range of movement.

The present invention resides in the combination, construction, arrangement, and disposition of various component parts and elements incorporated in the device in accordance with the principles of this invention. The present invention will be better understood and important features others than those specifically enumerated above will become apparent when consideration is given to the following details and description which, when taken in conjunction with the annexed drawings, describes, discloses, illustrates, and shows a preferred embodiment of the present invention and what is present considered and believed to be the best mode of practicing the principles of the invention. Other embodiments and modifications may be suggested to those having the benefit of the teachings herein, and such other embodiments and modifications are intended to be reserved, especially as they fall within the scope and spirit of the subjoined claims.

BRIEF DESCRIPTION OF THE DRAWINGS

In the accompanying drawings forming part of the specification, and in which like numerals are employed to designate like parts throughout the same.

FIG. 3 is an enlarged, partial cross-sectional view taken generally along the plane 3—3 in FIG. 1 but modified to show the instrument in the unactuated or released mode;

FIG. 4 is a partial cross-sectional view taken generally along the planes 4—4 in FIG. 3;

FIG. 5 is a cross-sectional view taken generally along the plane 5—5 in FIG. 3;

FIG. 6 is a fragmentary, enlarged, cross-sectional view taken generally along the plane 6—6 in FIG. 3;

FIG. 7 is a fragmentary, enlarged, cross-sectional view taken generally along the plane 7—7 in FIG. 3;

FIG. 8 is a fragmentary, enlarged, cross-sectional view taken generally along the plane 8—8 in FIG. 4;

FIG. 9 is an enlarged, cross-sectional view taken generally along the plane 9—9 in FIG. 3;

FIG. 10 is an enlarged, partial cross-sectional view taken generally along the plane 3—3 in FIG. 1 but modified to show the instrument in a fully released mode with a fastener having been ejected from the needle;

FIG. 11 is a fragmentary, partial cross-sectional view similar to FIG. 10 but showing only the rear portion of the instrument with the handle in the fully actuated position;

FIG. 12 is an enlarged, partial cross-sectional view taken along the planes 12—12 in FIG. 10 to show only the rear portion of the instrument in cross section;

FIG. 13 is a greatly enlarged cross-sectional view taken along the plane 13—13 in FIG. 11;

FIG. 14 is a greatly enlarged fragmentary cross-sectional view taken along the plane 14—14 in FIG. 10;

FIG. 15 is an exploded perspective view of the instrument but with the front housing pieces of the instrument rotated 90 degrees from the position illustrated in FIG. 1 to better illustrate the interior structure;

FIG. 16 is a view of the drive drum when viewed from the rear of the instrument;

FIG. 17 is a side view of the drive drum of FIG. 16 with a portion of the drum cut away to show the interior structure;

FIG. 18 is a fragmentary, plan view taken generally along the plane 18—18 in FIG. 17;

FIG. 19 is a view of one of the pieces comprising the internal housing of the instrument and showing integrally molded fixed ratchet teeth with the relative position of the drive drum of FIGS. 16-18 indicated by dashed lines; and FIG. 20 is a cross-sectional view taken generally along the plane 20—20 in FIG. 19 with the drive drum shown in dashed lines;

DESCRIPTION OF THE PREFERRED EMBODIMENT

This invention may be used in many different forms. This specification and the accompanying drawings disclose only one specific form as an example of the use of the invention. The invention is not intended to be limited to the embodiment illustrated, and the scope of the invention will be pointed out in the appended claims.

The precise shapes and sizes of the components herein described are not essential to the invention unless otherwise indicated.

For ease of description, the device of this invention will be described in an orientation as illustrated in the figures and terms such as upper, lower, horizontal, etc., will be used with reference to this orientation. It will be understood, however, that the device of this invention may be manufactured, stored, transported, used, and sold in an orientation other than the position described.

In the following description, reference is made to the industry standards of the American Iron and Steel Institute, 1000 16th Street, N.W., Washington, D.C. U.S.A. 20036. These standards will be designated by the common initial letters 37 AISI" followed by a suffix comprising additional alphanumeric characters and the standards are understood to be those in effect as of Aug. 1, 1981.

For ease of understanding the present invention, the invention is illustrated in a preferred embodiment comprising a hand-held, hand-operated device for closing a wound or incision in tissue with a particular type of fastener. Before describing in detail the various components of the fastener applier device, the fastener and the general method of applying the fastener with the device will first be described. This will be followed by a detailed description of the elements comprising the fastener applying device.

THE FASTENER

Figure 1:
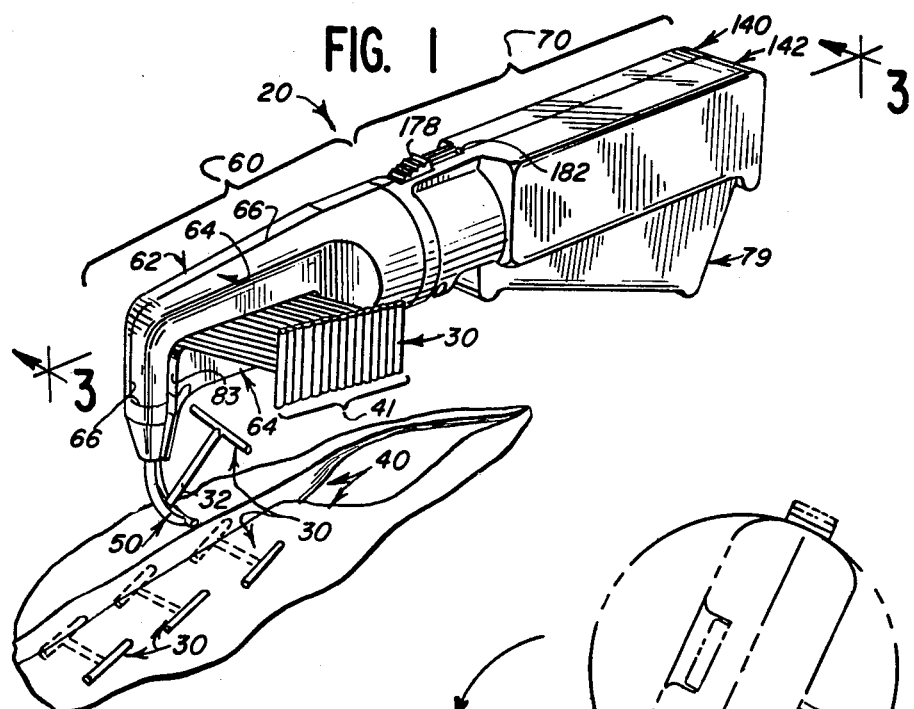
FIG. 1 is a perspective view of a hand-held surgical fastener applier instrument of the present invention shown being used to close an incision in tissue in a surgical procedure.

FIG. 1 illustrates a method of applying, with a fastener applier device 20 of the present invention, a plurality of fasteners 30 to skin or other tissue 40 in a surgical procedure.

The fastener 30 is identical to the flexible fastener disclosed in the U.S. Pat. No. 4,006,747 and reference is directed thereto for a complete description of such a fastener. Briefly, with reference to FIG. 2c of the drawings annexed hereto, the fastener 30 includes a filament member 32 terminated at one end by first anchoring means or rod-shaped head 36 and at the other end by an identical second anchoring means or rod-shaped head 34.

The fastener 30 is conveniently H-shaped and constructed of a flexible and resilient biocompatible material which may be either absorbable or non-absorbable in body tissue. As disclosed in detail in the above-referenced U.S. Pat. No. 4,006,747, the fastener 30 may be constructed of any of the wide variety of materials or combinations of materials. For example, materials such as nylon and polypropylene can be used to mold nonabsorbable fasteners 30 with good results. Also, copolymers of glycolide and lactide can also be used with good results and have the additional advantage of being absorbable in tissue and thus are particularly well suited for internal use in applications where long-term maintenance of wound support is not required.

As best illustrated in FIG. 1, a series of fasteners 30 are typically placed in close proximity along the length of the wound or incision to effectively close the wound or incision and enable natural healing to proceed. Non-absorbable fasteners are removed from the tissue closures by snipping off one head and withdrawing the fastener with the opposite head.

METHOD OF APPLYING THE FASTENER

Figure 2A:
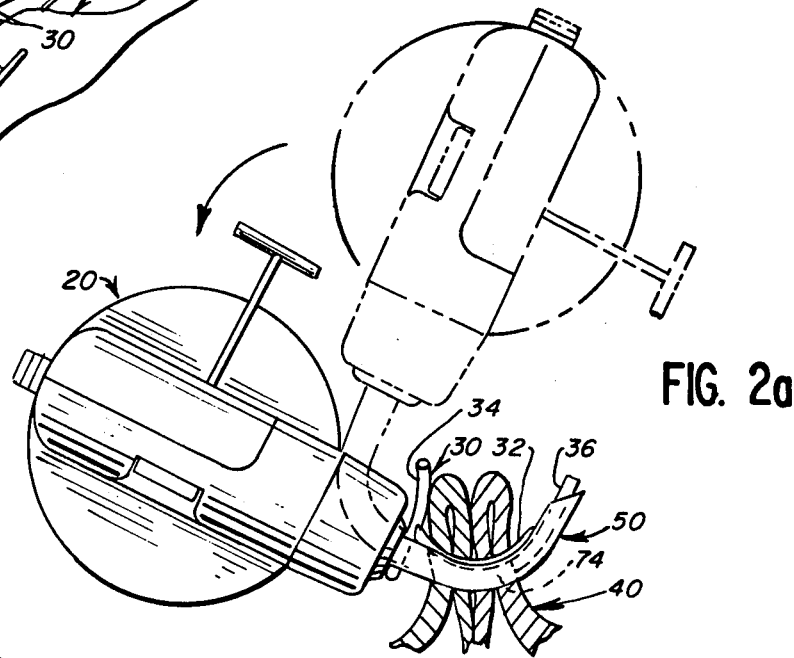
FIG. 2a is an end view of the fastener applier instrument of FIG. 1 and a fragmentary, cross-sectional view of the tissue with the instrument shown in dashed line in a first portion as the needle pierces the tissue and with the instrument shown in solid line in a moved position while placing a fastener across the incision.
Figure 2B:
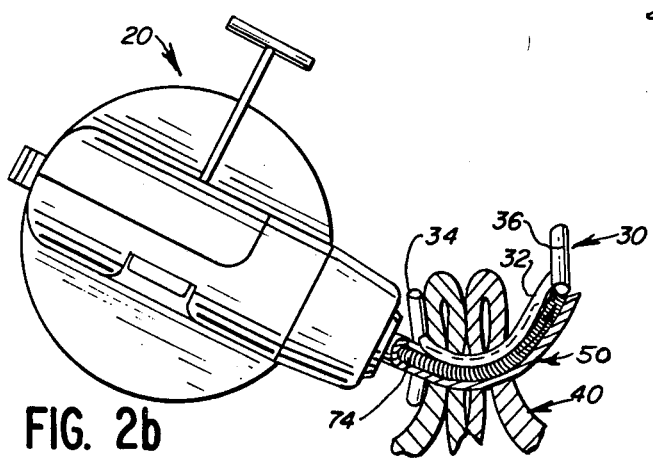
FIG. 2b is a view similar to FIG. 2a but showing a stage in the surgical procedure that is later than that illustrated in FIG. 2a and showing the needle in partial cross-section.
Figure 2C:
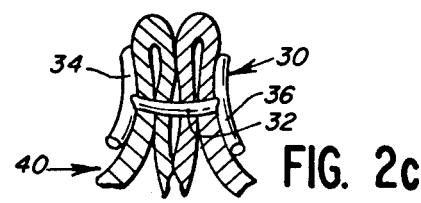
FIG. 2c is a fragmentary, cross-sectional view of the tissue after the fastener applier instrument has been removed so as to leave the fastener in place across the incision.

As best illustrated in FIG. 2c, and as more fully described in the above referenced U.S. Pat. No. 4,006,747, the fastener 30 is used to close a wound or incision by first folding over the tissue 40 on each side of the wound or incision and then approximating the folded over portions. Next, with the folded tissue held, as by grasping it with forceps, the flexible fastener 30 is temporarily bent or deformed and inserted through the skin on both the sides of the wound or incision. This can be effected with a fastener applying device, such as the device 20 illustrated in FIGS. 1-2b, in the general manner disclosed in the above-referenced U.S. Pat. No. 4,006,747.

Specifically, the device 20 is provided with means for holding a plurality of fasteners 30 in an aligned row 41 as best illustrated in FIG. 1. The device 20 includes a hollow needle 50 adapted for receiving one rod-shaped head of the fastener 30 as best illustrated in FIG. 1. The needle 50 also has a longitudinally extending slot through which the filament 32 of the fastener projects. The device 20 is adapted to feed one fastener 30 at a time into the hollow, slotted needle 50 and to push the fastener along the needle.

As best illustrated in FIG. 2a, the needle 50 is passed into the approximated and folded tissue 40 from a point on one side of the wound and on through the tissue until the tip of the needle 50 exits the tissue on the opposite side of the wound.

The path of the needle 50 through the tissue is not unlike that followed in conventional suturing. While closing a wound by conventional suturing, the needle and a length of attached suture are passed completely through the tissue. The hollow needle in the present case is inserted only far enough to penetrate through the tissue to form an open communication with both sides of the wound.

As best illustrated in FIGS. 2a and 2b, the applier device 20 includes a flexible pusher member 74 (visible in FIG. 2b) that is adapted to reciprocate within the curved, hollow needle 50 and to engage and push an end of the fastener's rod-shaped head 36 through the hollow needle 50 until it is discharged from the tip of the needle 50 on the far side of the wound. Then the needle 50 is withdrawn from the tissue while the fastener 30 is restrained in the tissue 40 by the head 36 on the far side of the wound. The fastener is thus left in the tissue 40 with the filament 32 of the fastener 30 traversing the wound along the path created by the needle 50 and with the two anchoring means (the heads 34 and 36) engaging and restraining the surface of the tissue 40 on either side of the wound or incision.

Although the needle 50 is illustrated in FIGS. 1-2b as being curved and as guiding a flexible pusher member 74, it is to be realized that the device 20 of the present invention may have a substantially straight needle for guiding the pusher member in a straight line if desired.

It has been found that when the needle 50 is curved and also projects downwardly and outwardly to one side of the fastener applier device 20 as illustrated in FIG. 1, certain advantages are realized. Specifically, the use of a needle having this type of orientation on the device 20 permits the surgeon to use a hand movement that is substantially similar to that used when applying conventional sutures with conventional suture needles. This is desirable since most surgeons have developed, and have become accustomed to, such hand movement when applying conventional sutures. Therefore, the adoption and use of the fastener applier device 20 of the present invention by a surgeon is more readily facilitated.

FIGS. 1-2c illustrate the tissue or skin 40 being folded over once at each side of the wound. It is to be realized that such a fold is not necessary when closing a wound or incision with the fastener 30 as installed by the fastener applier device 20 of the present invention. Specifically, reference is directed to FIGS. 2 and 4 of the above-discussed U.S. Pat. No. 4,006,747 for illustrations of the use of a fastener identical to the fastener 30 disclosed herein but wherein the tissue on each side of the wound is not folded over.

FASTENER APPLIER DEVICE MAGAZINE AND NEEDLE STRUCTURE

As best illustrated in FIG. 1, the device 20 has a generally elongate housing having a front or magazine portion 60 that contains the fastener row 41 and needle 50 and having a rear portion 70 that houses the actuating mechanism. A handle, trigger, or handle means 79 extends from the rear housing portion 70.

The first or front end portion 60 will next be described in detail with reference to FIGS. 1 and 3-5. With reference to FIG. 1, the front end portion 60 of the device preferably comprises two molded portions or pieces, piece 62 and piece 64. Each piece is preferably molded from a suitable material. For example, the pieces 62 and 64 may be molded from a polycarbonate resin such as that sold in the United States of America under the trademark or trade name Merlon M40 F by the Mobay Chemical Corporation.

Pieces 62 and 64 are mated together about a parting plane 66 (seen in FIG. 1 as the line running the length of the device 20). The pieces 62 and 64 are joined together by suitable means such as screws, adhesive, or other bonding means (not illustrated). In FIG. 3, the first piece 62 is viewed along its parting plane and is seen to define an arcuate channel 72 at the front end in which the flexible pusher member 74 is slidably disposed. The flexible pusher member 74 is preferably constructed from AISI 316 L Series stainless steel 30 gauge wire wound in a helical configuration having a radius slightly less than the radius of the arcuate channel 72.

The flexible pusher member 74 extends rearwardly in the device 20 from the front end of the housing magazine portion 60 through a hollow tube 78 into the rear portion 70 and is operatively engaged with the actuating means within the housing rear portion 70 as will be explained in detail hereinafter.

As best illustrated in FIGS. 1 and 4, the piece 64 of the housing front end portion 60 defines an L-shaped slot 83, the base leg portion of which L-shaped slot 83 is in registry with the arcuate channel 72 of the mating housing piece 62. The other leg of the L-shaped slot 83 receives the row 41 of fasteners 30.

The front end of the housing piece 62 has a generally conical configuration as best illustrated in FIGS. 1 and 5 and carries a needle holder insert 84 as best illustrated in FIG. 3. The needle holder insert 84 has a generally cylindrical configuration with a slot 86 in registry with the channel 72 of the housing piece 62.

The needle 50 is secured by a suitable means within the needle holder insert 84 and projects from the distal end thereof as best illustrated in FIGS. 3 and 5. The needle 50 is hollow and extends outwardly away from the housing piece 62. The distal end of the needle 50 is preferably angled or sharpened (as best illustrated in FIG. 2a) to facilitate the piercing of tissue.

The needle 50 defines a passage 80 as best illustrated in FIG. 5. The passage 80 extends along the length of the needle 50 from the entrance aperture of the needle within the needle holder insert 84 to the discharge aperture at the distal end of the needle 50. The needle 50 also defines a slot 82 along its length as best illustrated in FIG. 5. The slot 82 is coextensive with the passage 80 and therefore extends from the entrance aperture of the needle 50 within the needle holder insert 84 to the discharge aperture at the distal end of the needle 50. The slot 82 communicates with the passage 80 along the entire length of the needle 50. The passage 80 of the needle 50 is adapted to receive one of the fastener anchoring means or rod-shaped heads (head 36 in FIG. 2a). The slot 82 of the needle 50 is adapted to receive a portion of the filament 32 of the fastener 30.

In a preferred form of the invention illustrated, the needle 50 and the needle holder insert 84 are both preferably fabricated from a suitable metal, such as AISI 420 stainless steel. Preferably then the insert 84 and needle 50 are welded together to form an integral assembly which is then suitably secured within the conical portion of the housing piece 62.

As best illustrated in FIGS. 3 and 4, the front portion 60 of the fastener applier device 20 also includes a magazine 100 for holding a plurality of fasteners 30 in the row 41 and for feeding the fasteners 30 seriatim into the channel 72 defined in the front housing piece 62. Specifically, as best illustrated in FIGS. 3, 4, and 6, the magazine 100 includes a base member 102 defining a slot 103 and having a pair of angled retainer flanges 104 adapted to receive the fasteners 30. Specifically, the anchor means or rod-shaped head 36 of each fastener 30 is slidably received within the flanges 104 and on top of the slotted member 102. The fastener filament member 32 extends out of the magazine through the space defined between the flanges 104.

The magazine 100 is mounted within the housing portion 62 as best illustrated in FIGS. 3 and 4. Specifically, the rear end of the magazine 100 has a rearwardly extending tab 110 by which the magazine 100 is secured with a screw 112 to the housing portion 62. At the front end of the magazine 100, the magazine 100 has an off-set but forwardly extending tab 114 which is retained under a cross wall 116 of the housing portion 62.

Slidably disposed within the magazine 100 on top of the bottom member 102 is a feeder member 120 (FIGS. 4 and 7) which has a downwardly depending tab 122 disposed through the central slot 103 of the magazine bottom member 102.

The downwardly depending tab 122 of the feeder member 120 is biased forwardly with a band spring 126 as best illustrated in FIG. 4. As best illustrated in FIGS. 3, 7, and 8, the band spring has two oppositely coiled portions 130 which are disposed within a retainer or guide wall 132. The central portion of the band spring 126 is pulled outwardly from the coiled portions 130 and extends underneath and along the length of the magazine 100 to the feeder member tab 122 with which it is engaged. Thus, the feeder member 120 is continuously biased forwardly to push the fasteners 30 toward the channel 72 defined in the housing portion 62.

The guide tube 78, the arcuate channel 72 in the housing piece 62, and the channel 86 in the needle holder insert 84 all function as a guide means in the housing that serves to guide the movement of the flexible pusher member 74 into alignment with the entrance aperture and a passage 80 of the needle 50. Further, that portion of the channel 72 in the housing piece 62 immediately adjacent the front end of the magazine 100 can be regarded as defining a "fastener dispensing region" aligned with the entrance aperture of the needle 50 for accommodating admission of the fastener rod-shaped head 36 in registry or alignment with the entrance aperture and passage 80 (FIG. 5) of the needle 50.

As best illustrated in FIGS. 3 and 4, the width of the channel 72 in the housing portion 62 has a configuration and dimensions sufficient to accommodate the rod-shaped end of just one of the fasteners 30 at the front end of the magazine 100. The head 36 of the fastener is fed from the magazine 100 into the channel 72 just forward of the flexible pusher member 74 when the flexible pusher member 74 is in a fully retracted position. The channel 72 of the housing piece 62 thus serves to guide and align the flexible pusher member 74 and the rod-shaped head 36 of the fastener with the passage 80 of the needle 50. When the flexible member 74 is moved forwardly toward the needle 50 by suitable actuating means (described in detail hereinafter), the rod-shaped head 36 of the fastener 30 travels along the channel 72 of the housing portion 62, along the channel 86 of the needle holder insert 84, and finally through the needle 50. The flexible pusher member 74 is moved forwardly until its leading end pushes the fastener rod-shaped head 36 out of the needle passage 80 (as illustrated in detail in FIG. 2b).

After the rod-shaped head 36 of the fastener has been ejected from the needle discharge aperture, the flexible pusher member 74 is retracted back to the position illustrated in FIG. 3 (by means described in detail hereinafter). As long as the flexible pusher member 74 extends beyond the front of the magazine 100, the next fastener 30 in the magazine 100 is prevented from being fed from the magazine to the channel 72 in the housing piece 62. However, as soon as the flexible pusher member 74 has returned to a point just behind the magazine 100 as illustrated in FIG. 3, the next fastener 30 is urged forwardly into the channel 72 of the housing piece 62. Thus, the fastener applier device 20 is ready to apply the next fastener.

The magazine 100 is uniquely designed to prevent actuation of the instrument after all of the fasteners 30 have been ejected and when the magazine 100 is thus empty. Specifically, with continued reference to FIGS. 3 and 4, it can be seen that the forward or distal end portion of the feeder member 120 will project into the channel 72 after the last fastener has been ejected and after the flexible pusher member 74 has been fully retracted from the fastener dispensing region in front of the magazine 100. The fastener feeder member 120 will be maintained in this position at the forward end of the magazine by the band spring 126. Consequently, any attempt to move the flexible pusher member 74 forward from the fully retracted position illustrated in FIG. 3 will fail since the distal end of the flexible pusher member 74 will necessarily impinge against the end of the fastener feeder member 120 projecting into the channel 72. As will become evident hereinafter, this prevents the handle 79 from being actuated and thus serves as an indication that all of the fasteners have been ejected from the instrument.

REAR HOUSING AND ACTUATING HANDLE MOUNTING STRUCTURE

As best illustrated in FIGS. 3 and 4, the rear housing portion 70, which contains the actuating means and the handle or trigger 79, is fabricated from two halves or pieces 140 and 142. In FIG. 3, a forward part of the rear housing piece 140 is broken away along the parting plane to show the other rear housing piece 142. As best illustrated in FIGS. 3 and 4, the housing pieces 140 and 142 are suitably secured together, as with screws, one of which screws 144 is visible in FIG. 4. These pieces 140 and 142 are preferably molded from the same materials as the housing front portion 60 described above.

Preferably the handle or trigger 79 is molded from the same material as the other housing pieces and is pivotably mounted to the rear housing portion 70 about a pivot shaft 150 as illustrated in FIGS. 3, 10, and 12. The shaft 150 passes through the handle 79 as best illustrated in FIG. 12 and is journalled on either end in molded bearing structures 151 projecting inwardly from the rear housing pieces 140 and 142.

To operate the trigger 79, the device 20 is typically grasped with the palm of the hand at the top of the rear housing portion 70 (as viewed in FIG. 3) with the fingers and/or thumb extending down to the trigger 79. The trigger 79 is operably connected with an actuating means, described hereinafter in detail, to move the flexible pusher member 74 from the retracted position (illustrated in FIG. 3) to the extended position (illustrated in FIG. 2b) wherein the fastener 30 is ejected from the discharge aperture of the needle 50.

REAR HOUSING AND THE FRONT HOUSING ROTATION LATCH

As best illustrated in FIGS. 3 and 9, the rear housing piece 142 has a generally cylindrical portion 160 at the forward end of the rear housing. The cylindrical portion 160 is received in an annular flange 161 at the rear of the front housing piece 62. The cylindrical portion 160 has an aperture 163 through which the guide tube 78 passes. As best illustrated in FIGS. 3 and 4, the cylindrical portion 160 carries a retaining ring 164 in a groove for holding the cylindrical portion 160 within the flange 161 of the front housing piece 62. The ring 164 causes the rear housing pieces 140 and 142 to be biased forwardly with the cylindrical portion 160 until the rear housing pieces 140 and 142 engage the front housing pieces 62 and 64. This serves to hold together the rear housing 70 and front housing 60.

As best illustrated in FIG. 9, the annular portion of the front housing piece 62 includes a plurality of circumferential spaced bores 170. These bores 170 are adapted to receive an indexing pin 172 carried in a channel 174 of the rear housing piece 142. The indexing pin 172 is biased forwardly into one of the bores 170 by means of a compression spring 176 which is disposed within the bore 174 between the end of the bore and the indexing pin 172.

The indexing pin has an upwardly extending member or button 178 adapted to be engaged by the thumb of the surgeon operating the fastener applier device 20. As best illustrated in FIG. 1, the button 178 is adapted to reciprocate within a channel 182 defined in the mating housing pieces 140 and 142.

The front housing portion 60 and the rear housing portion 70 can be rotated relative to each other. Specifically, the front housing piece 62 (together with the front housing piece 64 connected to the piece 62) can be rotated together relative to the rear housing portion 70 about the cylindrical portion 160 when the indexing pin 172 is pulled rearwardly out of engagement with the bores 170. When the desired orientation of the needle 50, relative to the trigger 79, is obtained, the indexing pin 172 is released by the surgeon. The indexing pin 172 is then forced forwardly by the spring 176 against the front housing piece 62. An additional slight rotational movement of the front housing portion 60, in either direction of rotation, may be necessary to align one of the bores 170 with the indexing pin 172, whereupon the indexing pin 172 is driven further forwardly by the spring 176 into a bore 170 to thereby lock the front housing portion 60 relative to the rear housing portion 70.

THE ACTUATING MECHANISM

The rear housing portion 70 contains the novel actuating mechanism or means for reciprocating the flexible pusher member 74 between the retracted position and the extended position. The actuating mechanism is next described in detail with reference to FIGS. 10-20 which illustrate the interior structure of the rear housing portion 70 of the fastener applier device.

FIG. 10 shows the molded rear housing piece 142 viewed along its parting plane with some interior components cut away and with some interior components illustrated in cross section. For ease of illustration in FIG. 10, the front housing portion 60 has not been shown in cross section.

As best illustrated in FIGS. 10 and 12, the actuating mechanism includes an internal housing 300 disposed in the rear housing portion 70. As best illustrated in FIG. 15, the housing 300 includes two pieces, piece 301 and piece 302, which are adapted to be placed together in mating relationship and to contain between them various other components of the actuating mechanism described in detail hereinafter.

The internal housing pieces 301 and 302 may be secured to each other with suitable screws 309 (FIG. 12). To this end, the housing piece 301 is provided with appropriate screw receiving bores 310 (FIG. 15) and the housing piece 302 is provided with suitable threaded bores 312 (FIG. 15) aligned with the bores 310 of the housing piece 301. If desired, some of the bores 312 in the housing piece 302 may be unthreaded to permit the screws 309 to pass through the housing piece 302 and into suitable threaded bores 304 in the inwardly projecting bosses 307 (FIG. 15) of the rear housing piece 142. Of course, other suitable means may be provided for securing the housing pieces 301 and 302 together and/or for mounting the housing pieces 301 and 302 in the rear housing portion 70 of the device. Such other means may include snap-fit structures, rivets, adhesives, and the like.

Preferably, the internal housing pieces 301 and 302, and the internal components disposed therein, are molded from a thermoplastic polymer material to provide a lightweight assembly. For example, the housing pieces 301 and 302 may be molded from a polycarbonate resin such as that sold in the United States of America under the trademark or trade name Merlon M40 F by the Mobay Chemical Corporation.

As best illustrated in FIG. 10, the internal housing pieces 301 and 302 extend downwardly in the device and project into the handle 79. The handle 79 has a generally U-shaped cross section (as seen in FIGS. 14 and 15) so as to permit at least the lower portions of the internal housing 300 to be contained within the handle 79.

As best illustrated in FIG. 15, the internal housing piece 302 defines at its forward end a slot or channel 320 for receiving the rearward end of the guide tube 78 in which the flexible member 74 is slidably disposed. The flexible member 74 extends out of the rear end of the guide tube 78 and is received in a reduced diameter slot or channel 322 that is also defined in the housing piece 302. The rear end portion of the flexible pusher member 74 extends from the rearward end of the slot 322 and is secured to a rotatable drum 330 which is disposed within a cavity 332 in the housing piece 302.

As best illustrated in FIGS. 16 and 17, the drum 330 has a circumferential slot, channel or groove 334 which is adapted to receive a portion of the flexible pusher member 74 when the flexible pusher member is wound or wrapped around a portion of the circumference of the drum 330. The drum 330 has a generally cylindrical bore 336 merging with the circumferential groove 334 in which the distal end of the flexible pusher member 74 is received. The distal end of the flexible pusher member 74 is suitably secured within the bore 336, as with a suitable pin or adhesive (not illustrated).

Preferably, the drum 330 is molded as one piece from a synthetic polymer material such as that sold in the United States of America under the trademark or trade name Delrin 500 by the E. I. DuPont de Nemours & Company, Nemours Building, Wilmington, DE 19898.

As best illustrated in FIG. 16, the drum 330 also includes an annular hub 338 on one side defining a bore 339 and a pinion gear 340 on the other side. As best illustrated in FIGS. 12, 15, and 20, the drum 330 is disposed within the cavity or recess 332 of the housing piece 302 with the pinion 340 projecting through and beyond a cylindrical bore 333 in the housing piece 302.

The drum 330 preferably also includes a void region, cut out, or aperture 342 as best illustrated in FIG. 17. Extending into the aperture 342 is an arcuate arm 344 that includes at its distal end a laterally projecting pin 346 as best illustrated in FIGS. 16-18.

The drum hub 338 is received in a bore 350 of the housing piece 301 as best illustrated in FIGS. 15 and 20. Also, as best illustrated in FIGS. 19 and 20, the housing piece 301 also defines a circumferential array of ratchet gear teeth 352 which are adapted to engage the laterally projecting pin 346 of the drum 330. There are six teeth 352A, 352B, 352C, 352D, 352E, and 352F extending generally in a circular arc around the bore 350 of the housing piece 301. Specifically, with reference to FIG. 19, the ratchet teeth 352A-352F extend in a circular arc of about 265 degrees from a first tooth 352A to a last tooth 352F and define an inner guide surface or camming surface 354 around the bore 350. This leaves an arc of about 100 degrees of the circumference around the bore 350 free of ratchet teeth and camming surface 354. The major portion of the inner camming surface 354 has a generally circular arc configuration and the inner camming surface includes an inwardly angled surface 353 that extends to the exterior or outer surface of the last tooth 352F.

Owing to the arcuate configuration and inherent resiliency of the arm 344 on the drum 330, the pin 346 at the end of the arm 344 is cammed radially outwardly from a neutral position when the drum 330 is oriented to position the pin 346 adjacent the outer surfaces of any of the ratchet teeth. That is, in the position illustrated in FIG. 19, the pin 346 is being held by the teeth radially outwardly of its neutral, unbiased position by a small amount as illustrated in FIG. 17. Since the ratchet teeth are an integral, fixed part of the housing piece 301, the teeth will permit rotation of the drum 330 in a first direction (clockwise as viewed in FIG. 19 or counterclockwise as viewed in FIG. 10). However, the teeth will prevent rotation of the drum 330 in the opposite or second direction (counterclockwise as viewed in FIG. 19 or clockwise as viewed in FIG. 10) until the instrument is first fully actuated as will be explained in detail hereinafter.

A novel mechanism is associated with the handle 79 for rotating the drum 330 to move the flexible pusher member 74 from the retracted position (wherein the leading end of the pusher member 74 is located behind the dispensing region to permit a fastener to be moved into the dispensing region in alignment with the needle entrance aperture) and an extended position (wherein the leading end of the pusher member 74 is engaged with a fastener for ejecting the fastener from the needle discharge aperture). Specifically, a gear segment 369 (FIGS. 10-12) is provided to mesh with the teeth of the pinion 340 and is mounted at its lower end by means of a pin 372 (FIGS. 10 and 11) to the handle 79.

When the handle 79 is squeezed upwardly from the released or unactuated position illustrated in FIG. 10 to the fully actuated position illustrated in FIG. 11, the gear segment 369 rotates the pinion 340 to cause rotation of the drum 330 in a first direction (counterclockwise in the direction of arrow 376 as illustrated in FIG. 11). This causes forward movement of the flexible member 74, along the guide channel 322 of the internal housing piece 302, from the retracted position to the extended position.

As best illustrated in FIGS. 10, 12, and 15, a spring 370 is provided to bias the handle 79 from the fully actuated position (FIG. 11) to the unactuated or released position (FIG. 10). Specifically, the spring 370 is wound around the pivot shaft 150 and has two upper legs 372 (FIGS. 12 and 15) forming a U-shaped structure bearing against the bottoms of the two housing pieces 301 and 302. The spring 370 also has two lower legs 374 bearing against the inside bottom portion of the handle 79. Thus, when the actuated handle 79 is released, the spring 370 acts to force the handle from the actuated position (FIG. 11) to the unactuated or released position (FIG. 10). However, owing to the engagement of the drum pin 346 with the fixed ratchet teeth 352A-352F as described above, the handle 79 will not be biased to the released position by the spring 370 unless and until the handle 79 is first moved completely to the fully actuated position as illustrated in FIG. 11. In this fully actuated position, the drum pin 346 has been carried (counterclockwise as viewed in FIG. 10) just beyond the end of the last tooth 352F so that it is free to spring radially inwardly a small amount to its neutral position adjacent the inwardly angled surface 353 of the last ratchet tooth 352F (only FIGS. 10 and 19 show the angled surface 353).

Next, under the influence of the spring 370, the handle 79 is then forced outwardly from the instrument toward the released position. This causes rotation of the drum and pin 346 (clockwise as viewed in FIG. 10 or counterclockwise as viewed in FIG. 19). The drum 330 thus rotates in the second direction and carries the laterally extending pin 346 against the angled surface 353 of the last ratchet tooth 352F which deflects the pin 346 radially inwardly from its neutral position so that the pin 346 follows the circular, inner camming surface 354 along the inside of the ratchet teeth.

When the handle 79 reaches the fully released position (FIG. 10), a lip 381 (FIG. 10) engages the rear housing portion 70 and terminates the movement of the handle 79 and of the drum 330. When the handle 79 is in the fully released position, the drum 330 has rotated the pin 346 to a point just past the first ratchet tooth 352A. Thus, the pin 346 is free to be moved radially outwardly a small amount by the natural spring action of the arm 344 until the pin 346 is again in its neutral position. At this point, the pin 346 is in registry with the outer surface of the first tooth 352A. Consequently, when the handle 79 is again moved to the actuated position (FIG. 11), the drum 330 rotates the pin 346 (counterclockwise as viewed in FIG. 10 and clockwise as viewed in FIG. 19) against the outside surface of the first tooth 352A and subsequently along the outside surfaces of all of the teeth. When the pin 346 is engaged with the surfaces of the teeth, the handle 79 cannot be pivoted by the spring 370 to the fully actuated position unless and until the handle 79 is first moved to the fully actuated position (FIG. 11) wherein the laterally projecting pin 346 is again moved past the last tooth 352F at the end of the circular arc of ratchet teeth.

The above-described pin and ratchet mechanism thus functions as a full stroke compelling mechanism and prevents return of the handle 79 to the released position until the instrument has been fully actuated. Further, this prevents more than one fastener 30 from being pushed through the needle 50 at one time since the pusher member 74 cannot be retracted past the fastener magazine 100 to engage a second fastener until the first fastener is ejected.

Although the entire actuating mechanism described above is particularly useful when incorporated in the fastener applier device 20 for applying fasteners 30, it is to be realized that the actuating mechanism may be incorporated in other instruments. Such other instruments may have flexible pusher members for pushing a foreign body, other than a fastener, into tissue.

Also, such other instruments may instead incorporate one or more other types of movable operating elements or members actuated by, or connected to, a flexible pusher member secured to the rotatable drum. Such other instruments may include instruments for applying ligating clips to blood vessels, bone crushing instruments, pin cutting instruments, and instruments for applying staples to tissue.

From the foregoing, it will be observed that numerous variations and modifications may be effected without departing from the true spirit and scope of the novel concept of the invention. It is to be understood that no limitation with respect to the specific apparatus and method illustrated herein is intended or should be inferred. It is, of course, intended to cover by the appended claims all such modifications as fall within the scope of the claims.

What is claimed is:

1. An actuating mechanism for a hand-operated surgical instrument for applying a plurality of fasteners to tissue, said instrument having at least one moveable operating member, said actuating mechanism placing said fasteners in the tissue, said mechanism comprising:

a drum mounted for rotation relative to said instrument; said drum including an arm biased to a neutral position and including a laterally projecting pin extending from said arm; said arm adapted to be moved radially inwardly and radially outwardly relative to the axis of rotation of said drum;

a flexibe pusher member engaging, extending from, or functioning as said operating member; said flexible pusher member being secured to said drum for being wound at least partially around the circumference of said drum;

means for guiding said flexible pusher member for reciprocating movement adjacent said drum;

means for rotating said drum in a first direction for unwinding said flexible pusher member from said drum to move said flexible pusher member relative to said instrument from a retracted position to an extended position for effecting movement of said operating member;

means for rotating said drum in a second direction to return said flexible pusher member to said retracted position; and an array of fixed teeth adjacent said drum and extending generally in a circular arc about an axis coincident with the axis of rotation of said drum; said teeth having an exterior tooth surface for engaging said laterally projecting pin and deflecting said pin and arm radially outwardly when said drum is rotated in said first direction; said teeth defining an inner camming surface for deflecting said pin and arm radially inwardly and permitting rotation of said drum in said second direction only after said pin has been rotated in said first direction past the end of said circular arc array of ratchet teeth.

2. The mechanism in accordance with claim 1 in which said instrument includes an external housing, in which said actuating mechanism includes an internal housing mounted within said external housing, in which said drum is mounted within said internal housing, and in which said teeth are formed as part of said internal housing.

3. The mechanism in accordance with claim 1 in which said means for rotating said drum in said first and second directions includes at least (1) a handle pivotally mounted to said instrument; (2) a gear segment mounted to said handle; and (3) a pinion gear extending from said drum, rotatable with said drum, and engaged with said gear segment whereby pivoting movement of said handle toward said instrument rotates said drum in said first direction and pivoting movement of said handle away from said instrument rotates said drum in said second direction.

4. The mechanism in accordance with claim 1 in which said drum includes an arcuate aperture located between the circumferential edge of the drum and the center of the drum; in which said arm is an arcuate member extending into said aperture in a plane normal to the axis of rotation of said drum; and in which said pin projects laterally from the end of said arm in a direction generally parallel with said axis of rotation of said drum.

5. The mechanism in accordance with claim 1 in which said teeth extend in said arc about said axis of rotation of said drum for about 265°.

6. The mechanism in accordance with claim 1 in which said array of teeth is defined at one end by a first tooth and at the other end by a last tooth.

7. The mechanism in accordance with claim 6 in which said inner camming surface includes a portion having a circular arc configuration merging with an inwardly angled surface that extends to the outer surface of said last tooth.

* * * * *